United States Patent [19]

Spector et al.

[11] Patent Number: 5,578,597
[45] Date of Patent: Nov. 26, 1996

[54] COMBINATION THERAPY FOR HIV INFECTION

[75] Inventors: Reynold Spector, Scotch Plains, N.J.; Paul J. Deutsch, Sea Cliff, N.Y.; Alan Nies, Scotch Plains, N.J.

[73] Assignee: Merck & Co., Inc., Rahway, N.J.

[21] Appl. No.: 505,842

[22] Filed: Jul. 21, 1995

Related U.S. Application Data

[63] Continuation of Ser. No. 135,706, Oct. 13, 1993, abandoned.
[51] Int. Cl.$^6$ .................................................. A61K 31/495
[52] U.S. Cl. ........................................ 514/255; 514/400
[58] Field of Search ...................................... 514/255, 400

[56] References Cited

PUBLICATIONS

Brockmeyer et al 1988, Clinical Immunol Immunopathol vol. 48(1) pp. 50–60–Med Abstract–AIDSline Document#: Med–88253871.

Primary Examiner—Russell Travers
Attorney, Agent, or Firm—Roy D. Meredith; Jack L. Tribble

[57] ABSTRACT

The combination of the HIV protease inhibitor L-735,524 and one of ketoconazole or cimetidine is useful in the inhibition of HIV protease, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

5 Claims, No Drawings

COMBINATION THERAPY FOR HIV INFECTION

This is a continuation of application Ser. No. 08/135,706, now abandoned, filed on Oct. 13, 1993.

BACKGROUND OF THE INVENTION

This case is related to Merck case U.S. Pat. No. 5,413,999.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., Proc. Nat'l Acad. Sci. 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compound L-735,524 is a potent inhibitor of HIV protease and is useful in the treatment of AIDS or ARC, without substantial side effects or toxicity.

Applicants have discovered that administration of L-735,524 may require dosing as frequently as every four hours. To solve this problem, a combination therapy for AIDS has been discovered by applicants.

Applicants demonstrate that the combination of compounds of this invention is an effective inhibitor of HIV protease.

In the present invention, applicants co-administer a potent HIV protease inhibitor, such as L-735,524 or other chemical entities, with ketoconazole or cimetidine. This combination therapy is a method to enhance the pharmacokinetics of the HIV protease inhibitor which may have a short serum half-life due to rapid metabolism by $P_{450}$ isozymes. Cimetidine and ketoconazole are inhibitors of $P_{450}$ isozymes.

BRIEF DESCRIPTION OF THE INVENTION

The combination in this invention is useful in the inhibition of HIV protease, the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with the combination of certain compounds, or pharmaceutically acceptable salts thereof, in the inhibition of HIV protease, the prevention or treatment of infection by HIV and in the treatment of the resulting acquired immune deficiency syndrome (AIDS). The combination is defined as follows:

L-735,524 and an inhibitor of $P_{450}$ isozymes selected from ketoconazole and cimetidine, or pharmaceutically acceptable salts thereof.

The HIV protease inhibitor L-735,524 is synthesized by the protocol of Merck Case 18597Y, EP 0541168, published 12 May 1993, which is U.S. Pat. No. 5,413,999 herein incorporated by reference. The compound L-735,524 is N-(2(R)-hydroxy-1(S)-indanyl)-2(R)-phenylmethyl-4-(S)-hydroxy-5-(1-(4-(3-pyridylmethyl)-2(S)-N'-(butylcarboxamido)-piperazinyl))-pentaneamide, or pharmaceutically acceptable salt thereof.

Ketoconazole is cis-1-acetyl-4-[4-[[2-(2,4-dichlorophenyl)-2-(1H-imidazol-1ylmethyl)-1,3-dioxolan-4-yl]-methoxy]phenyl]-piperazine or pharmaceutically acceptable salt thereof. It is synthesized by the procedures of U.S. Pat. No. 4,144,346 or U.S. Pat. No. 4,223,036, both incorporated by reference for these purposes.

Cimetidine is N-cyano-N'-methyl-N"-[2-[[(5-methyl-1H-imidazol-4-yl)methyl]thio]ethyl]guanidine, or pharmaceutically acceptable salt thereof. It is synthesized by the procedures of U.S. Pat. No. 3,950,333, incorporated by reference for this purpose.

The pharmaceutically-acceptable salts of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The combination of compounds of the present invention is useful in the inhibition of HIV protease, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

For these purposes, the combinations of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of each compound in the combination of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered to humans in the dosage ranges specific for each compound. L-735,524 or pharmaceutically acceptable salt thereof is administered orally in a dosage range between about 40 mg and about 4000 mg per day, divided into between one and four doses per day. Ketoconazole or pharmaceutically acceptable salt thereof is administered orally at a dosage range between about 200 mg every other day and about 400 mg twice a day. Cimetidine or pharmaceutically acceptable salt thereof is administered orally or i.v. at a dosage range between about 100 mg and about 4800 mg per day, divided into between one and four doses per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLE 1

Protocol for Pharmacokinetic Evaluation of Combination Therapy with Only Cimetidine A. This is a fixed-sequence, randomized, four period, parallel protocol to measure the effect of cimetidine on the pharmacokinetics and safety and tolerability of L-735,524, an HIV-1 protease inhibitor in seronegative patients. The pharmacokinetics and safety of a single 400 mg oral dose of L-735,524 is measured at baseline (Period I) and again (Period II) following administration of cimetidine 600 mg bid (or a placebo instead of cimetidine) for six days. After an additional day of cimetidine (or placebo) administration, to distinguish between effects of cimetidine related to the inhibition of gastric acid secretion and effects related to other mechanisms such as the inhibition of cytochrome $P_{450}$ metabolism, L-735,524 is administered with a low cola beverage and plasma concentration profile of L-735,524 again measured (Period Ill). In the first three periods, to minimize the hypochlorhydria resulting from administration of cimetidine, L-735,524 is administered in the morning with the last dose of cimetidine/placebo administered twelve hours previously and the subsequent A.M. cimetidine dose administered two hours following L-735,524. In a fourth period on the following day, L-735,524, 400 mg, is taken 90 minutes after a 300 mg i.v. cimetidine, to more directly assess the effects of increased gastric pH. The study design is outlined in detail in the Table. Plasma concentration of L-735,524 is determined at 0, 0.25, 0.5, 0.75, 1, 1.5, 2, 3, 4, 6, 8, 10 and 12 hours following each of the four doses. Laboratory safety is measured at predose and 12 hours after L-735,524 on Day 1, prior to L-735,524 on Days 8, 9, and 10 and 24 hours after the last dose of L-735,524 (on Day 11).

Total plasma clearance of L-735,524 is calculated as the dose divided by the total area under the plasma concentration-time curve from zero to infinity. The apparent half-life is estimated from the slope of the terminal phase fitted to the log plasma concentration-time curve by the method of least squares. The concentration of L-735,524 in plasma or plasma filtrate is determined by analysis on HPLC, monitored for absorbance at 220 nm.

TABLE

| | |
|---|---|
| Period I (day O) Period I (day 1)- L-735,524 pharmacokinetics | L-735,524 single 400 mg dose plasma profile (12 h) |
| Period I-to-II- interim treatment (days 2–7) | cimetidine 600 mg bid each day, on day 7 repeat caffeine breath test |
| Period II-L-735,524 pharmacokinetics (day 8) | Repeat L-735,524 single 400 mg dose plasma profile while continuing cimetidine 600 mg bid |
| Period III- L-735,524 pharmacokinetics (day 9) | Administer L-735,524 single 400 mg dose with low pH cola and repeat L-735,524 plasma profile, while continuing cimetidine 600 mg bid |

TABLE-continued

| Period IV L-735,524 pharmacokinetics (day 10) | Administer L-735,524 single 400 mg dose 90 min following 300 mg cimetidine i.v. and repeat L-735,524 plasma profile |

EXAMPLE 2

Protocol for Combination Therapy with Only Cimetidine

B. In this protocol to show the antiviral activity of one regimen of L-753,524 given with cimetidine in HIV-seronegative subjects, L-735,524 is administered at a dose of 300 mg three times a day and cimetidine is administered at 800 mg once a day. Antiviral activity is measured before and during combination therapy by measuring serum levels of the HIV p24 antigen, serum levels of HIV RNA, and CD4 lymphocyte counts.

EXAMPLE 3

Protocol for Pharmocokinetic Evaluation of Combination Therapy with Only Ketoconazole This is a protocol to show effects of ketoconazole on plasma concentration profile of L-735,524 in HIV-seronegative subjects. It is a fixed-sequence, randomized, two-period, parallel protocol. The pharmacokinetics and safety of a single oral dose L-735,524 is measured at baseline (Period I) and again (Period II) following administration of ketoconazole at 200 mg once a day (or a placebo instead of ketoconazole) for six days.

EXAMPLE 4

Protocol for Combination Therapy with Only Cimetidine

In this protocol to show the antiviral activity of one regimen of L-735,524 given with ketoconazole in HIV-seronegative subjects, L-735,524 is administered at a dose of 300 mg three times a day and ketoconazole is administered at 200 mg once a day. Antiviral activity is measured before and during combination therapy by measuring serum levels of the HIV p24 antigen, serum levels of HIV RNA, and CD4 lymphocyte counts.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. The composition comprising the combination of compounds, which is ketoconazole and N-(2(R)-hydroxy-1(S)-indanyl)-2(R)-phenylmethyl-4-(S)hydroxy-5-(1-(4-(3-pyridylmethyl)-2(S)-N'-(t-butylcarboxamido)-piperazinyl))-pentaneamide, or pharmaceutically acceptable salt thereof.

2. A method of inhibiting HIV protease, comprising administering to suitable mammal in need of such treatment an effective amount of the composition of claim 1.

3. A method of preventing infection of HIV, or of treating infection by HIV or of treating AIDS or ARC, comprising administering to a suitable mammal in need of such treatment an effective amount of the composition of claim 1.

4. A pharmaceutical composition useful for inhibiting HIV protease, comprising an effective amount of the composition of claim 1, and a pharmaceutically acceptable carrier.

5. A pharmaceutical composition useful for preventing or treating infection of HIV or for treating AIDS or ARC, comprising an effective amount of the composition of claim 1, and a pharmaceutically acceptable carrier.

* * * * *